United States Patent
Sherman et al.

(10) Patent No.: US 8,667,963 B2
(45) Date of Patent: Mar. 11, 2014

(54) VENTILATOR CIRCUIT FOR OXYGEN GENERATING SYSTEM

(75) Inventors: Leslie H. Sherman, Denville, NJ (US); George Beck, Mendham, NJ (US)

(73) Assignee: IMPACT Instrumentation, Inc., West Caldwell, NJ (US)

( * ) Notice: Subject to any disclaimer, the term of this patent is extended or adjusted under 35 U.S.C. 154(b) by 1618 days.

(21) Appl. No.: 11/803,528

(22) Filed: May 15, 2007

(65) Prior Publication Data

US 2007/0272243 A1    Nov. 29, 2007

Related U.S. Application Data

(60) Provisional application No. 60/800,913, filed on May 16, 2006.

(51) Int. Cl.
*A61M 16/12* (2006.01)
*A61M 16/10* (2006.01)
*A61M 16/00* (2006.01)

(52) U.S. Cl.
USPC ............ 128/205.11; 128/204.21; 128/204.18; 128/200.24; 128/205.24

(58) Field of Classification Search
USPC ............ 128/201.21, 202.26, 204.18, 204.23, 128/204.26, 205.25, 200.24, 201.13, 128/204.17, 205.23
See application file for complete search history.

(56) References Cited

U.S. PATENT DOCUMENTS

| | | | | |
|---|---|---|---|---|
| 4,883,051 A | * | 11/1989 | Westenskow et al. ... | 128/204.21 |
| 5,365,922 A | * | 11/1994 | Raemer .................... | 128/204.23 |
| 5,404,873 A | * | 4/1995 | Leagre et al. ............ | 128/204.18 |
| 5,660,171 A | * | 8/1997 | Kimm et al. ............. | 128/204.23 |
| 6,253,765 B1 | * | 7/2001 | Hognelid et al. ........ | 128/204.18 |
| 6,269,810 B1 | * | 8/2001 | Brooker et al. .......... | 128/203.12 |
| 6,823,866 B2 | * | 11/2004 | Jafari et al. ............. | 128/204.21 |
| 2005/0109340 A1 | * | 5/2005 | Tehrani .................... | 128/204.21 |

* cited by examiner

*Primary Examiner* — Annette Dixon
(74) *Attorney, Agent, or Firm* — Gerald E. Hespos; Michael J. Porco; Matthew T. Hespos

(57) ABSTRACT

A ventilator circuit is provided for use with a ventilator and a low pressure low flow oxygen source to provide a hyperoxygenated mixture of air and oxygen at the onset of inspiration. The ventilator circuit achieves this result by using its inspiratory limb to store oxygen between breaths. As a result, the oxygen content of dead space gas is increased before delivery to the distal alveoli of the patient. Accordingly, the ventilator circuit achieves an efficient use of available oxygen and requires less oxygen to a desired oxyhemoglobin percentage at the patient.

8 Claims, 6 Drawing Sheets

VENTILATOR CIRCUIT FOR OXYGEN GENERATING SYSTEM

This application claims priority on U.S. Provisional Patent Appl. No. 60/800,913, filed May 16, 2006.

BACKGROUND OF THE INVENTION

1. Field of the Invention

The invention relates to a ventilator circuit for use with a low pressure low flow oxygen generator that by design requires less oxygen to achieve a desired oxyhemoglobin percentage at the patient as compared to conventional means of oxygen delivery.

2. Description of the Related Art

The respiratory and/or circulatory systems of many patients may not be sufficiently viable to sustain the patient with oxygen levels that exist in ambient air. A typical ventilator system contains a means to deliver ambient or compressed air to a patient. The ventilator typically has means to accept oxygen from a high pressure or low pressure source and to vary the mixture of air and oxygen. A ventilator circuit communicates with the ventilator and the patient. The ventilator circuit provides a conduit for the gas or gas mixture to be delivered cyclically to the patient and then to be exhaled by the patient. The ability to have high pressure oxygen available in sufficient volume is not always possible or practical. In most hospitals, liquid oxygen is converted to a gas, pressurized, and made available via a piped system to wall outlets located throughout the facility. This source of oxygen supply is plentiful and generally is available at all times unless there is a power failure or generating system failure. Hospitals maintain a limited supply of oxygen that is stored in cylinders for intra-hospital transport and backup use in the event that the primary system fails. High pressure oxygen that is stored in cylinders is delivered through a pressure reducing regulator. When full, the cylinder stores compressed oxygen at about 2200 PSI. Cylinders are available in various sizes, and the size determines the oxygen storage volume and the degree of portability. The cylinder size can impose handling constraints on the caregiver and mobility constraints on the patient. Reliance on oxygen cylinders also can present a risk if resupply is not available. Accordingly, oxygen generators may be considered an alternative way to provide higher concentrations of oxygen. A ventilator circuit is required to provide communication between the ventilator and the patient and acts as a conduit for the gas or the gas mixture to be delivered to the patient and then exhaled by the patient. Low pressure low flow oxygen generators are sufficient for many applications and often are the only practical alternative. Examples of low pressure low flow oxygen generators include oxygen concentrators, chemical oxygen generators, oxygen therapy regulators connected to a nominal 50 PSI source and ceramic oxygen generators. Oxygen concentrators can rely upon positive pressure swing adsorption or positive/negative pressure swing adsorption. Chemical oxygen generators can be solid generators or solid/liquid generators. Some oxygen generators can be controlled to cycle "on" and "off" as needed. Other oxygen generators, once activated, remain "on" until their chemical reaction is exhausted.

Low pressure/low flow oxygen generators typically have an output of less than 10 liters per minute with five-six liters per minute being the most common.

The typical prior art ventilator circuit, by design, is incompatible for direct use with oxygen enrichment devices. Instead, oxygen is mixed with air or is delivered unmixed by the ventilator and through the ventilator circuit to the patient in a sufficient volume to meet the needs of the patient. Another less common method is to direct a continuous low flow rate of oxygen to a reservoir that communicates with the compressor intake of a ventilator. The ventilator cycles "on" to deliver a breath via the ventilator circuit. As a result, the reservoir content is delivered to the patient along with supplemental air if needed. In the former example, the oxygen percentage is set at the ventilator and delivered to the patient via the ventilator circuit. In the latter example, the percentage to be delivered is measured by an oxygen monitor at the connection between the output of the ventilator and the input of the ventilator circuit. Adjustments to the oxygen flow rate into the reservoir are made until the desired mixture is being sent from the ventilator to the patient. The typical prior art ventilator circuit permits inspiration gas to be delivered to the patient and exhaled gas to be conducted away from the patient. This inflow and outflow of gas is embodied in ventilator circuits that have single limb, dual limb and coaxial designs. The circuit includes a patient connection that is configured for connection with a mask or endotracheal tube that will be placed directly in communication with the patient.

In use, the patient will inhale the oxygen rich gas that flows through the ventilator circuit. The patient then will exhale and the exhaled gas will flow mostly through the ventilator circuit and out the exhalation valve. The exhalation valve is either part of the ventilator circuit or part of the ventilator, depending on whether the circuit design is a single limb, a dual limb or coaxial. A portion of the exhaled gases, including carbon dioxide, will remain in the ventilator circuit. As a result, the next inspiration cycle will start with that portion of the remaining gases, including the carbon dioxide being delivered to the patient. Accordingly, the oxygenation process will exhibit less than optimum efficiencies, and it may be necessary to provide a higher percentage of oxygen with each successive breath to compensate for the remaining gases of the previous breath. This can quickly deplete a limited supply of oxygen.

A system that could control the appropriate flow of oxygen to a patient would achieve several significant advantages. For example, approximately one-third of the volume of gas that is delivered to the patient never gets to the lungs distal alveoli because it never gets past the upper respiratory tract area. This area generally is known as "dead space" where no gas exchange takes place. Thus, a ventilator circuit that is capable of prefilling itself with a higher concentration of oxygen to be delivered at the front end of a breath and ambient air at its back end will ensure (i) that a higher concentration of oxygen will reach the distal alveoli, (ii) that mostly ambient air will wind up in the dead space area, and (iii) the use of less oxygen, by volume, can provide effective oxygenation equivalent to that of a greater volume of oxygen used in a conventional manner. In yet another example, the oxygen generator could be smaller, or for any given size, the oxygen generator could require replacement or maintenance less frequently due to a lower demand on its output capability. Accordingly, it is an object of the subject invention to provide a ventilator circuit that can be used with a ventilator and a low pressure low flow oxygen generator to provide more efficient use of the oxygen generator.

SUMMARY OF THE INVENTION

The invention relates to a ventilator circuit for use with a ventilator that is operative to deliver oxygen or an air/oxygen mix to a patient at a low pressure and low flow rate. The ventilator circuit includes an inspiratory line that can be placed in communication with the ventilator for delivering the inspiratory gas (e.g. air/oxygen mix) to the patient. An oxygen fill enable valve communicates with the inspiratory line for controlling the flow of gas through the inspiratory line and towards the patient. The ventilator circuit may further include a patent connection that communicates with an outlet end of the inspiratory line. The patient connection preferably is configured for connecting to the patient via a mask or an endotracheal tube. An exhalation valve communicates with the inspiratory line and with the patient connection and is operative for selectively permitting a release of gas that is exhaled by the patient. Pressure sensing means may be provided between the patient connection and the exhalation valve and may communicate with circuitry of the ventilator for sensing pressure conditions indicative of the stages in the respiratory cycle. The ventilator receives data from the pressure sensing means and produces signals for controlling the opening and closing of both the oxygen fill enable valve and the exhalation valve to control a flow of the air/oxygen mix through the inspiratory line and towards the patient connection at appropriate stages during the respiratory cycle.

The ventilator circuit includes or communicates with a low pressure low flow source of oxygen. More particularly, an oxygen fill line extends from the low pressure low flow oxygen source and communicates with the inspiratory line at a location between the oxygen fill enable valve and the exhalation valve, and preferably at a location close to the exhalation valve. A one way check valve is incorporated into the inspiratory line between the oxygen fill line and the exhalation valve. The check valve permits the low pressure low flow oxygen to fill the inspiratory line without venting through the exhalation valve during exhalation cycles. The check valve also seals off a leak path that might otherwise exist through the oxygen fill enable valve during the exhalation cycle. As a result, exhaled air containing carbon dioxide does not flow into the inspiratory line during the exhalation cycle. Rather, oxygen from the low pressure low flow oxygen source is permitted to flow through the oxygen fill line and into the inspiratory line during exhalation cycles. A second check valve permits directional gas flow from the low pressure low flow oxygen source to pass through the oxygen fill line into the inspiratory line and prevents gas from flowing from the inspiratory line into the oxygen fill line, particularly if a low pressure low flow oxygen source is not connected.

The disposition of the oxygen fill enable valve and the exhalation valve change during the inspiration cycle so that the air oxygen mix can flow to the patient connection. However, the initial flow of gas to the patient at the start of the inspiratory cycle is the gas that resides in the inspiratory line at the end of the expiration cycle. Unlike the prior art system described above, the subject ventilator circuit ensures that the initial flow of gas to the patient during the inspiratory cycle is sufficiently rich in oxygen due to the flow of oxygen from the low pressure low flow oxygen source through the oxygen fill line and into the inspiratory line during the exhalation cycle. As a result, the patient is assured of achieving an air oxygen mix that is appropriately rich in oxygen during the first two thirds of the inspiratory cycle where it matters the most.

The ventilator circuit can be adapted for any of the available ventilators or any ventilators that may be developed. The ventilator circuit can be a single limb circuit with or without pneumotach connecting tubes. In this system, the oxygen fill enable valve and the exhalation valve are arranged substantially linearly along the inspiratory line. Another variation of this design includes a "wye" connection so that the exhalation valve is offset from the inspiratory line. Additional ventilator circuit variations can be of the dual limb style or a dual lumen style circuit where the exhalation valve communicates with the patient connection via a separate line or via a separate lumen in a dual lumen line. The oxygen fill enable valve and the exhalation valve may be part of the ventilator circuit and separate from the ventilator. Alternatively, the oxygen fill enable valve and/or exhalation valve may be part of the ventilator.

The ventilator circuit, ventilator and low pressure low flow oxygen source may be used in communication with a peripheral pulse oximeter or in combination with a peripheral pulse oximeter and capnograph along with software algorithm or other computer program product to form a closed-loop oxygen controller that optimizes the amount of oxygen that is stored between breaths and to optimally maintain a patient's oxyhemoglobin or oxyhemoglobin and end tidal carbon dioxide within preset parameters

DETAILED DESCRIPTION OF THE PREFERRED EMBODIMENTS

Figure 1:
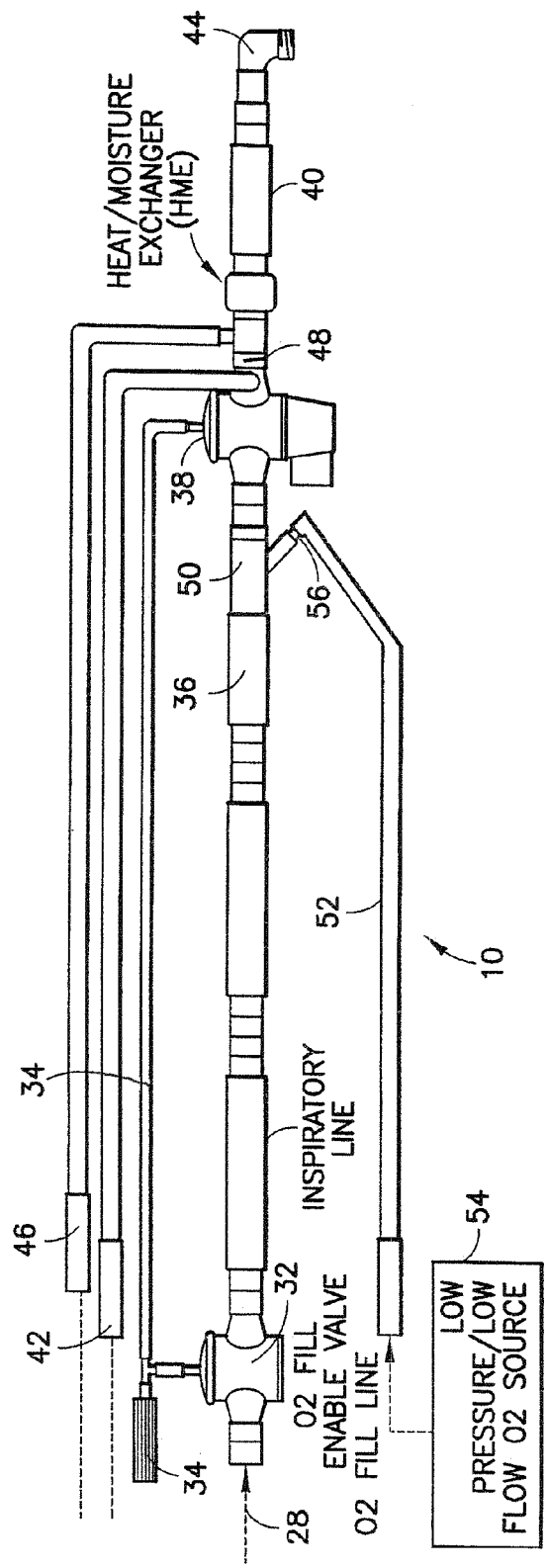
FIG. 1 is a schematic diagram of a single limb ventilator circuit in accordance with the subject invention.
Figure 2:
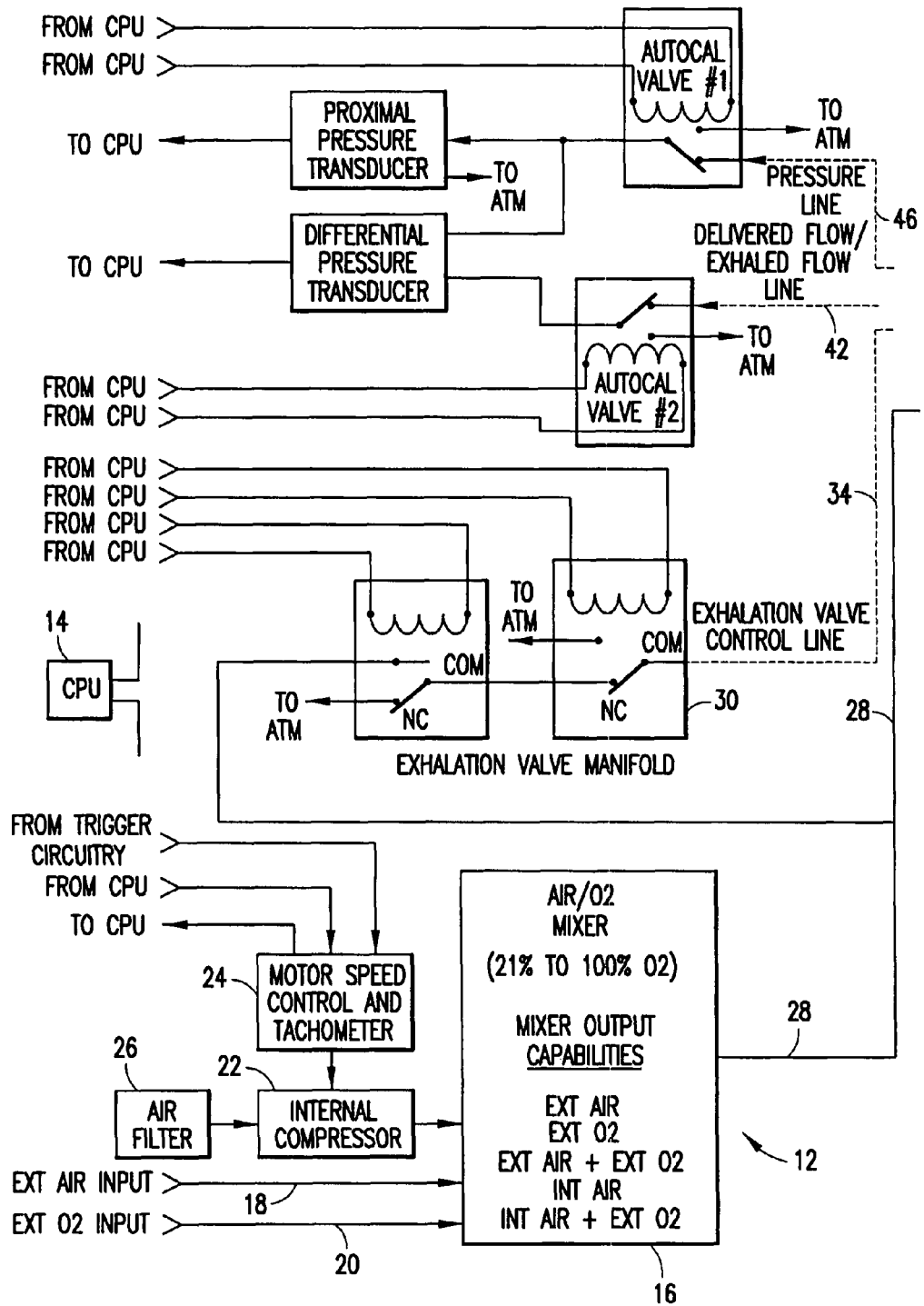
FIG. 2 is a schematic view of a ventilator for use with the ventilator circuit of FIG. 1.

A first embodiment of a ventilator circuit in accordance with the subject invention is identified generally by the numeral 10 in FIG. 1. The ventilator circuit 10 is used with a ventilator 12 as shown in FIG. 2. More particularly, the ventilator 12 of FIG. 2 includes a CPU 14 that controls the operation of the ventilator 12 and its ventilator circuit 10. The ventilator 12 is operative to deliver an air/O2 mixture to the ventilator circuit 10. More particularly, an air/O2 mixer 16 is incorporated into the ventilator 12 and may be controlled by signals generated by the CPU 14. The air/O2 mixer 16 includes an external air input 18 and an external O2 input 20 that communicate respectively with supplies of external air and oxygen. The CPU settings determine the proportion of air and oxygen to create the desired mixture. The air input to the air/O2 mixer 16 can be driven by an internal compressor 22 rather than an external air supply. In this case, a motor speed control and tachometer 24 communicates with the internal compressor 22 and further communicates with the CPU 14 to proportion the air and oxygen to obtain the desired mixture. Thus, the CPU 14 receives speed data from the motor speed control and tachometer 24 for indicating the speed of the internal compressor 22. Additionally, the CPU 14 can generate signals to the motor speed control and tachometer 24 for controlling the speed of the internal compressor 22. The internal compressor 22 further communicates with an air filter 26 for filtering air that is inputted to the air/O2 mixer 16. The air/O2 mixer 16 further includes an output line 28 that delivers the mixture of air and O2 to the ventilator circuit 10 as described further herein. The output line 28 further communicates with an exhalation valve manifold 30 that is operative to generate pneumatic signals for operating valves of the ventilator circuit 10 as described further herein. Other configurations of the ventilator 12 can be used with ventilator circuit 10.

The first embodiment of the ventilator circuit 10, as shown in FIG. 1, includes an O2 fill enable valve 32 that communicates with the outlet line 28 from the air/O2 mixer 16. The O2 fill enable valve 32 also communicates with an exhalation valve control line 34 that extends from the exhalation valve manifold 30 of the ventilator 12.

An inspiratory line 36 extends from the O2 fill enable valve 32 and is operative for delivering the air/O2 mixture from the ventilator 12 towards the patient. In the embodiment of FIG. 1, an exhalation valve 38 is connected to the end of the inspiratory line 36 at a position remote from the O2 fill enable valve 32. The exhalation valve 38 further communicates with a patient connection 40 and with a delivered flow/exhale flow line 42. The outlet end 44 of the patient connection 40 remote from the exhalation valve 38 is configured for connection to the patient via a mask or endotracheal tube (not shown). A pressure line 46 extends from the patient connection 40 at a location between the outlet end 44 of the patient connection 40 and the delivered flow/exhale flow line 42. A delivered flow/exhale flow means for creating a small pressure drop 48 is disposed in the patient connection 40 between the delivered flow/exhale flow line 42 and the pressure line 46.

A first check valve 50 is incorporated into the inspiratory line 36 between the O2 fill enable valve 32 and the exhalation valve 38 and in close proximity to the exhalation valve 38. The first check valve 50 is a one way check valve.

The ventilator circuit 10 further includes an O2 fill line 52 that extends from a low pressure low flow oxygen source 54 to a location on the inspiratory line 36 between the O2 fill valve 32 and the first check valve 50 and substantially adjacent to the check valve 50. A second check valve 56 is incorporated into the O2 fill line 52 and allows the ventilator circuit 10 to work if there is no low pressure/low flow source connected.

The exhalation valve control line 34 of the ventilator 12 communicates with both the O2 fill enable valve 32 and the exhalation valve 38 and receives pneumatic signals from the exhalation valve manifold 30 for operating the O2 fill valve 32 and the exhalation valve 38.

In operation, the O2 fill enable valve 32 normally is open and allows oxygen fill gas from the O2 fill line 52 to fill the inspiratory line 36 during the exhalation cycle. Pressure from the exhalation valve control line 34 closes the O2 fill enable valve 32 during the inspiratory cycle and the patient will inhale the air/oxygen mix that has accumulated in the inspiratory line 36 during the previous exhalation cycle. During the exhalation cycle, the exhalation valve 38 permits the exhaled air to exit from the ventilator circuit 10.

As noted above, the mechanical characteristics of the ventilator permit some of the exhaled air to accumulate in the inspiratory line of the prior art system and the subject invention. As a result, each subsequent inspiratory cycle in the prior art system and the subject invention permits part of the most recently exhaled gas to be inhaled again by the patient. This retention of exhaled gas in the ventilator circuit also adds to the exhaled volume that is simultaneously retained in the patient's anatomical dead space. In the prior art, this effect is mitigated partially by designs that reduce circuit dead space. Whereas the prior art delivers a breathing gas mixture for each successive breath that consists of essentially a uniform mixture, approximately one-third of the oxygen used to create this mixture never gets to the distal alveoli in the lungs where gas exchange actually takes place. In contrast, the subject invention hyper-oxygenates the part of the inspiratory line 36 that is closest to the patient to raise the O2 content of the retained gas more effectively by mixing with it in the anatomical dead space on its way to the distal alveoli during the next inspiratory cycle.

Figure 3:
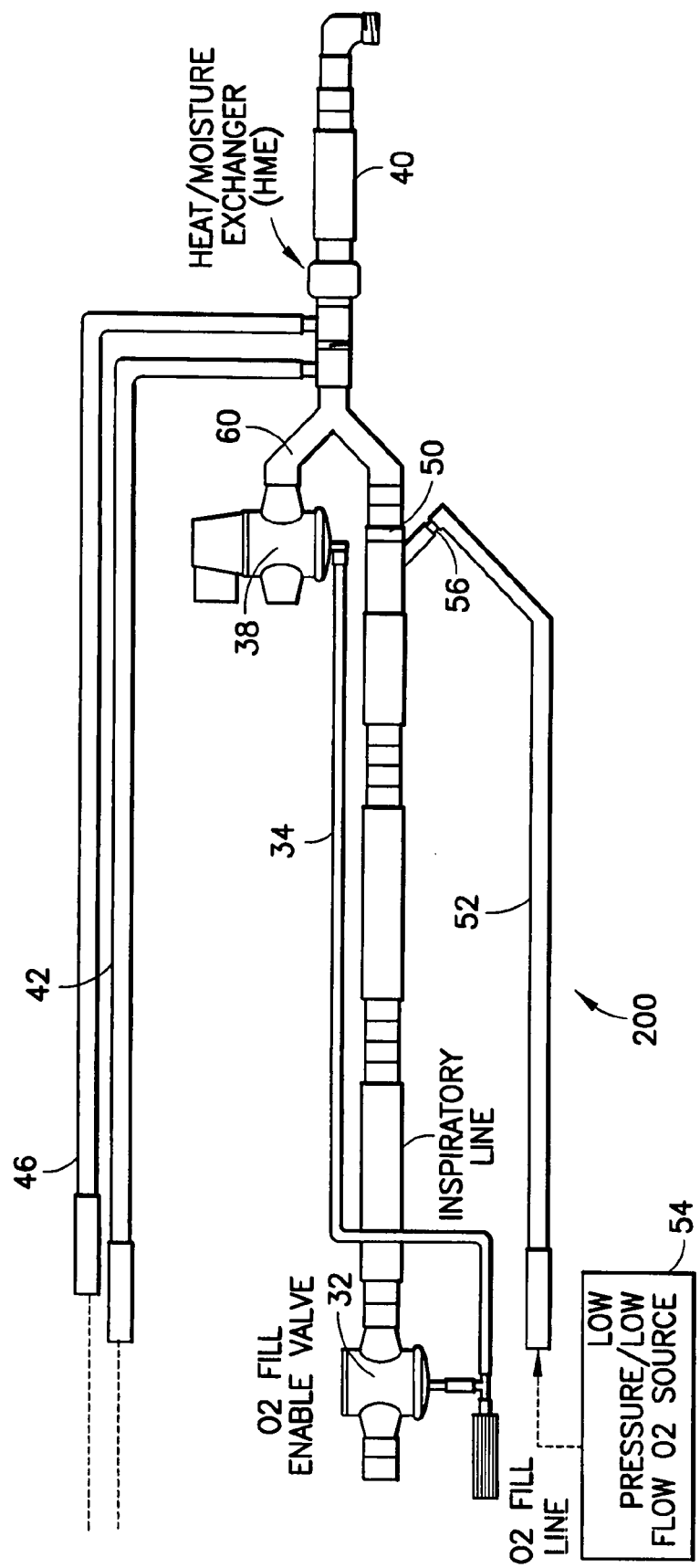
FIG. 3 is a schematic diagram of a single limb ventilator circuit in accordance with the subject invention and incorporating a wye connection to the exhalation valve.

FIG. 3 shows an alternate embodiment of the ventilator circuit identified generally by the numeral 200. This design typically has less circuit dead space than the single limb circuit design of FIG. 1. More particularly, the ventilator circuit 200 is a single limb ventilator circuit similar to the ventilator circuit 10 described above with respect to the FIG. 1. However, the ventilator circuit 200 includes a wye fitting 60 between the check valve 50 and the patient connection 44. The exhalation valve 38 then is connected to one branch of the wye fitting 60, and hence is in an off line position from the inspiratory line 36. All other aspects of the ventilator circuit 200 shown in FIG. 2 are substantially the same as in the FIG. 1 embodiment. Furthermore, the ventilator circuit 200 of FIG. 2 achieves the same functional advantage of filling the inspiratory line 36 with oxygen that flows through the O2 fill line 52 from the low pressure low flow O2 source 54. Hence, the patient is assured of receiving the proper volume of oxygen at the start and throughout each inspiration cycle.

Figure 4:
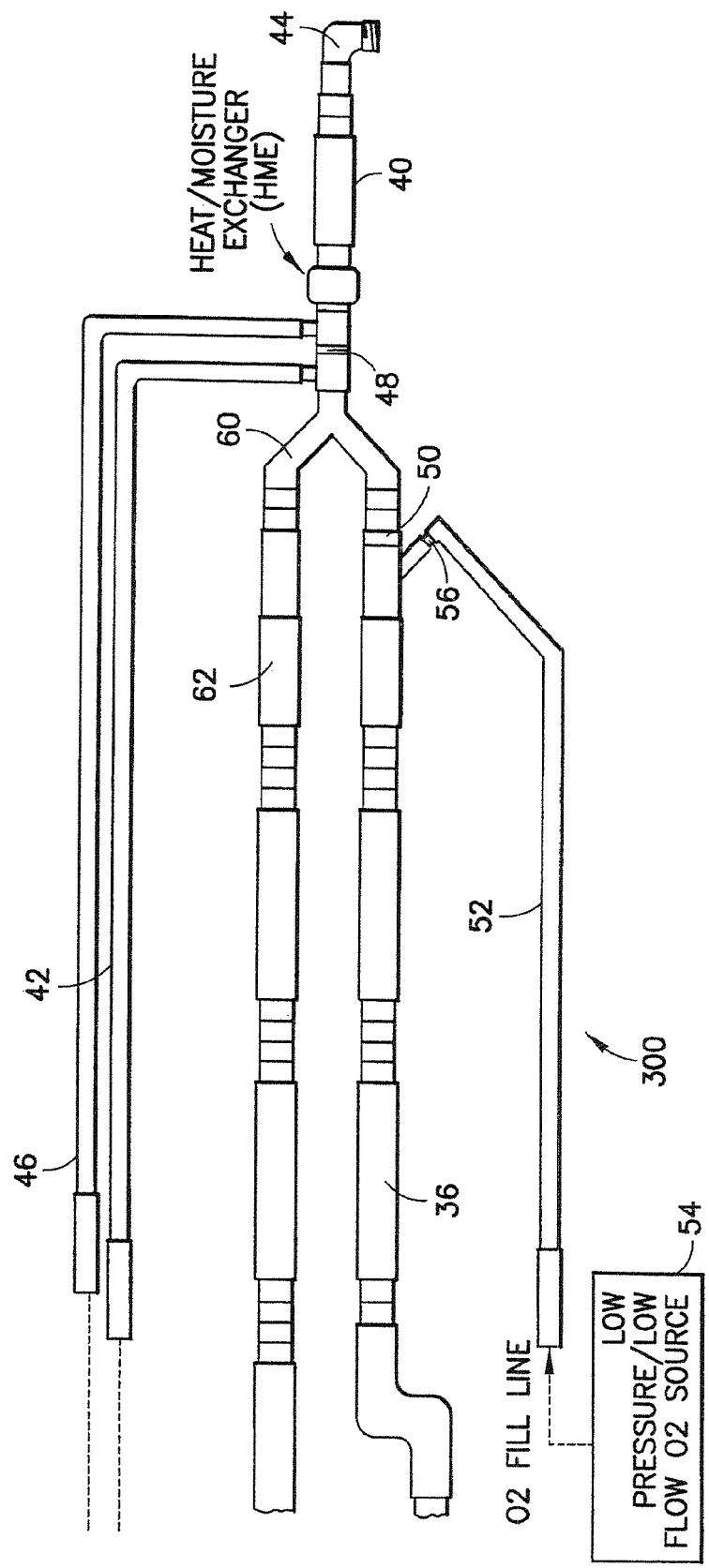
FIG. 4 is a schematic diagram of a dual limb ventilator circuit in accordance with the invention.
Figure 5:
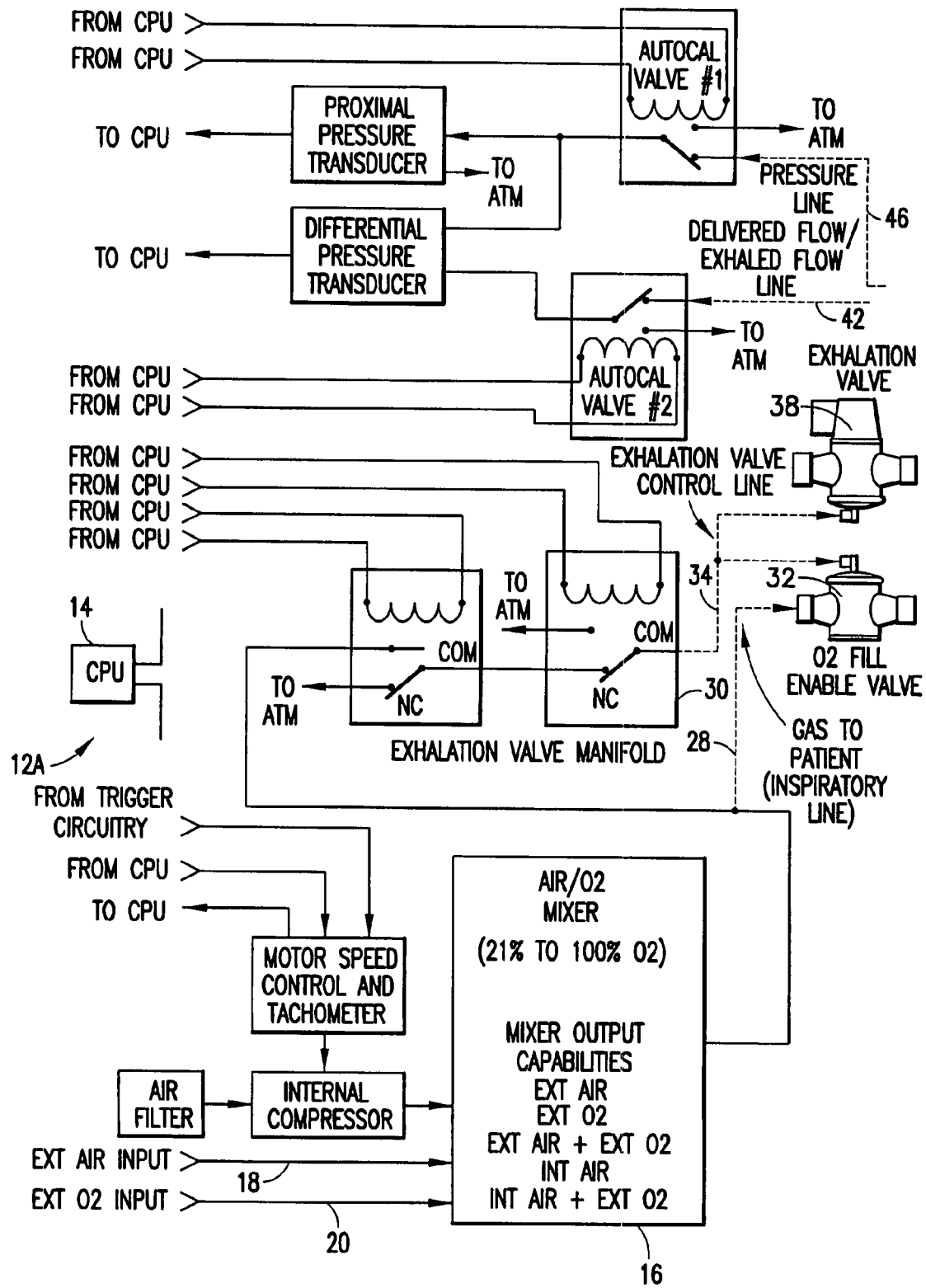
FIG. 5 is a schematic view of a ventilator for use with the ventilator circuit of FIG. 4.

FIGS. 4 and 5 show a third embodiment of the ventilator circuit. The ventilator circuit of FIG. 4 is a dual limb circuit and is identified generally by the numeral 300 in FIG. 3. The FIG. 4 embodiment is structurally and functionally very similar to the FIG. 2 embodiment. In particular, a wye fitting 60 is in substantially the same position depicted in the FIG. 2 embodiment. However, the FIG. 4 ventilator circuit 300 further includes an expiratory line 62 that extends from wye fitting 60 to the exhalation valve 38. This embodiment further has the O2 fill enable valve 32 and the exhalation valve 38 as being parts of the ventilator 12A, as shown in FIG. 5. However, the ventilator circuit 10 and the ventilator 12A cooperate to function substantially the same as in the first two embodiments.

Figure 6:
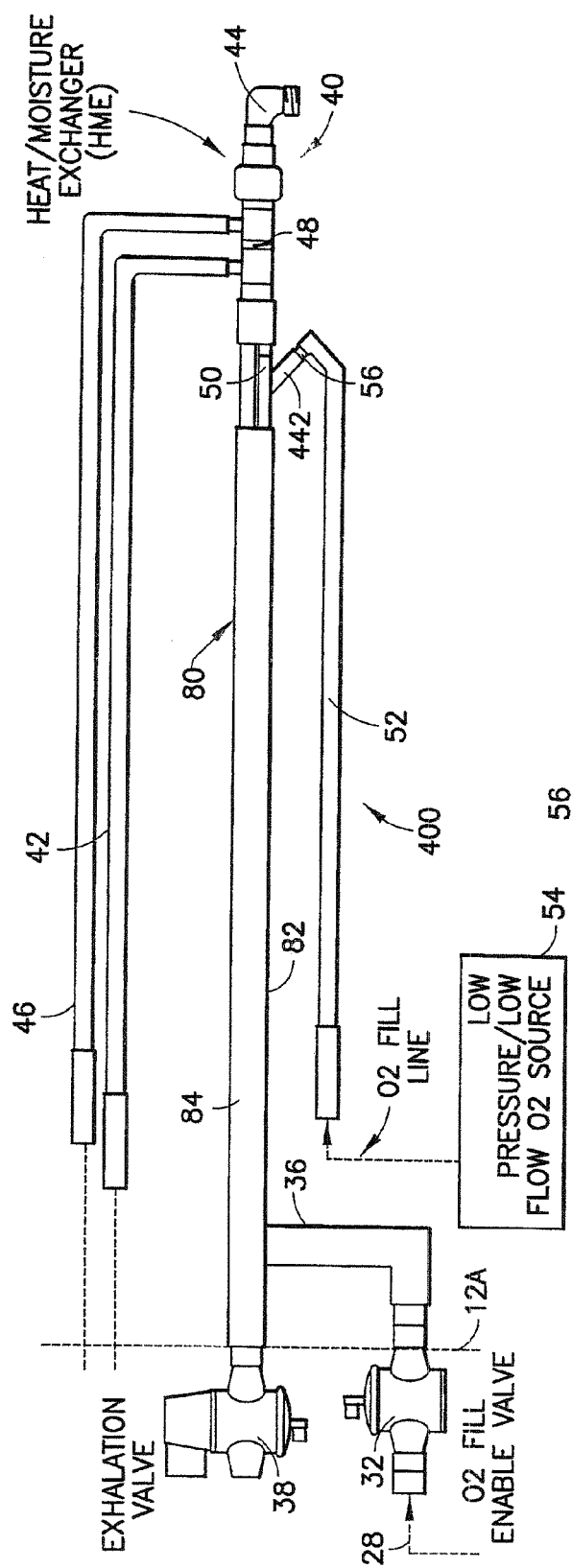
FIG. 6 is a schematic diagram of a dual lumen ventilator circuit in accordance with the invention.

FIG. 6 shows a further variation of the ventilator circuit, and specifically depicts a dual lumen circuit identified generally by the numeral 400. In particular, the ventilator circuit 400 of FIG. 6 has a dual lumen line 80 with an inspiratory segment 82 and an expiratory segment 84. The inspiratory segment 82 of the dual lumen line 80 extends from the O2 fill enable valve 32 to the patient connector 40. The expiratory segment 84 of the dual lumen line 80 extends substantially from the patient connection 40 to the exhalation valve 38. The check valve 42 is disposed in the inspiratory segment 82 in proximity to the patient connection 44. The O2 fill line 52 communicates with the inspiratory segment 82 at a location near the check valve above the check valve 442 and between the check valve 50 and the O2 fill enable valve 32. The ventilator circuit 400 of FIG. 6 functions exactly the same as the ventilator circuit 300 as shown in FIG. 3.

What is claimed is:

1. A ventilator circuit for use with a ventilator to provide a mixture of air and oxygen to a patient that receives oxygen from a low pressure low flow supply, the ventilator circuit comprising:

a fill enable valve for selectively enabling the flow of gas including a replenishing supply of oxygen from the ventilator;

an inspiratory line extending from the fill enable valve towards the patient;

an exhalation valve in communication with an end of the inspiratory line remote from the fill enable valve, the exhalation valve being operable for selectively opening and accommodating a flow of gas from the inspiratory line to the patient and selectively closing and blocking a flow of gas from the inspiratory line to the patient and allowing an outflow of exhaled gas from the patient downstream of the exhalation valve; and an oxygen fill line extending from a low pressure low flow supply of oxygen and into communication with the inspiratory line at a location near the exhalation valve, whereby oxygen from the oxygen fill line can fill the inspiratory line during an exhalation cycle performed by the ventilator with the exhalation valve closed.

2. The ventilator circuit of claim 1, further comprising a one way check valve in the inspiratory line between the oxygen fill line and the exhalation valve for enabling oxygen from the oxygen fill line to substantially fill the inspiratory line during the exhalation cycle without venting through the exhalation valve.

3. The ventilator circuit of claim 2, further comprising a check valve in the oxygen fill line and oriented to permit the ventilator circuit to operate without leaking if the low pressure low flow oxygen is disconnected from the oxygen fill line.

4. The ventilator circuit of claim 2, further comprising a patient connector communicating with the end of the inspiratory line remote from the ventilator for delivering gas to the patient and for accommodating gas to be exhaled from the patient through the exhalation valve.

5. The ventilator circuit of claim 4, further comprising a wye fitting having a first leg communicating with the end of the inspiratory line remote from the fill enable valve, a second leg connected to the patient connection and a third leg communicating with the exhalation valve.

6. The ventilator circuit of claim 5, further comprising an exhalation line extending from the third leg of the wye fitting to the exhalation valve.

7. The ventilator circuit of claim 6, further comprising a dual lumen line having first and second lumen therein, the first lumen defining a portion of the inspiratory line, the second lumen defining a portion of the exhalation line.

8. A ventilator circuit for use with a ventilator and a low pressure low flow oxygen source, the ventilator circuit comprising:

a fill enable valve for selectively enabling a flow of gas from the ventilator and the low pressure low flow oxygen source;

an inspiratory line extending from the fill enable valve towards a patient; and an oxygen fill line extending from a low pressure low flow supply of oxygen to a location in the inspiratory line between the fill enable valve and the patient to use the inspiratory line to store oxygen between breaths, whereby the ventilator circuit provides a hyper-oxygenated mixture of air and oxygen to the patient at the onset of inspiration.

* * * * *